(12) United States Patent
Czibula et al.

(10) Patent No.: US 8,569,496 B2
(45) Date of Patent: Oct. 29, 2013

(54) PIPERAZINE SALT AND A PROCESS FOR THE PREPARATION THEREOF

(75) Inventors: Laszlo Czibula, Budapest (HU); Eva Againe Csongor, Pomaz (HU); Katalin Nogradi, Budapest (HU); Balint Juhasz, Torokbalint (HU); Ferenc Sebok, Mezokovacshaza (HU); Janos Galambos, Budapest (HU); Istvan Vago, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 0 days.

(21) Appl. No.: 13/140,232

(22) PCT Filed: Dec. 17, 2009

(86) PCT No.: PCT/HU2009/000108
§ 371 (c)(1),
(2), (4) Date: Jul. 27, 2011

(87) PCT Pub. No.: WO2010/070369
PCT Pub. Date: Jun. 24, 2010

(65) Prior Publication Data
US 2011/0275816 A1    Nov. 10, 2011

(30) Foreign Application Priority Data
Dec. 17, 2008    (HU) .................................. 0800763

(51) Int. Cl.
*C07D 295/135*    (2006.01)
(52) U.S. Cl.
USPC .......................................... 544/392; 544/395
(58) Field of Classification Search
USPC .................................................. 544/392, 395
See application file for complete search history.

(56) References Cited

U.S. PATENT DOCUMENTS

| | | | |
|---|---|---|---|
| 4,957,921 A | 9/1990 | Caprathe et al. | |
| 5,846,514 A | 12/1998 | Foster et al. | |
| 6,334,997 B1 | 1/2002 | Foster et al. | |
| 6,489,341 B1 | 12/2002 | Jerussi | |
| 6,528,529 B1 | 3/2003 | Brann et al. | |
| 6,566,550 B2 | 5/2003 | Lowe, III | |
| 6,919,342 B2 | 7/2005 | Haupt | |
| 7,122,576 B2 | 10/2006 | Plata-Salaman et al. | |
| 7,737,142 B2 | 6/2010 | Csongor et al. | |
| 7,829,569 B2 | 11/2010 | Liao et al. | |
| 7,875,610 B2 | 1/2011 | Szalai et al. | |
| 7,943,621 B2 | 5/2011 | Czibula et al. | |
| 7,981,897 B2 | 7/2011 | Bathe et al. | |
| 2003/0144285 A1 | 7/2003 | Brann et al. | |
| 2004/0259882 A1 | 12/2004 | Haupt et al. | |
| 2005/0107397 A1* | 5/2005 | Galambos et al. | 514/255.03 |
| 2006/0229297 A1 | 10/2006 | Csongor et al. | |
| 2007/0259885 A1 | 11/2007 | Bathe et al. | |
| 2010/0137335 A1 | 6/2010 | Csongor et al. | |
| 2010/0197666 A1 | 8/2010 | Laszlovsky et al. | |
| 2010/0197667 A1 | 8/2010 | Laszlovsky et al. | |
| 2010/0256145 A1 | 10/2010 | Bak-Jensen et al. | |
| 2011/0059980 A1 | 3/2011 | Oobayashi | |
| 2011/0112093 A1 | 5/2011 | Szalai et al. | |
| 2011/0269959 A1 | 11/2011 | Csongor et al. | |
| 2011/0275804 A1 | 11/2011 | Czibula et al. | |

FOREIGN PATENT DOCUMENTS

| | | |
|---|---|---|
| EP | 0431580 | 3/1995 |
| WO | WO 97/11070 | 3/1997 |
| WO | WO 99/50247 | 10/1999 |
| WO | WO 99/67206 | 12/1999 |
| WO | WO 01/05763 | 1/2001 |
| WO | WO03029233 | 4/2003 |
| WO | WO 03/064393 | 8/2003 |
| WO | WO 2005/012266  * | 2/2005 |
| WO | WO2005012266 | 2/2005 |
| WO | WO 2006/082456 | 8/2006 |
| WO | WO 2007/033191 | 3/2007 |
| WO | WO 2008/139235  * | 11/2008 |
| WO | WO 2008/141135 | 11/2008 |
| WO | WO 2008/142461 | 11/2008 |
| WO | WO 2010/009309 | 1/2010 |

OTHER PUBLICATIONS

Jun Han "Trends in Bio/Pharmaceutical Industry", 3 (2006); p. 25-29.*

(Continued)

*Primary Examiner* — Noble Jarrell
*Assistant Examiner* — Valerie Rodriguez-Garcia
(74) *Attorney, Agent, or Firm* — Fish & Richardson P.C.

(57) ABSTRACT

The invention relates to novel trans N-{4-{2-[4-(2,3-dichlorophenyl)-piperazine-1-il]-ethyl}-cyclohexylamine dihydrochloride monohydrate and a process for the preparation of the trans N-{4-{2-[4-(2,3-dichlorophenyl)-piperazine-1-il]-ethyl}-cyclohexylamine dihydrochloride monohydrate, said process comprising the steps
a) reacting trans 2-{1-[4-(N-tert-butoxycarbonyl)amino]-cyclohexyl}-acetic acid ester with sodium borohydride and aluminum trichloride to give trans 2-{1-[4-(N-tert-butoxycarbonyl)-amino]-cyclohexyl}-ethanol;
b) reacting trans 2-{1-[4-(N-tert-butoxycarbonyl)-amino]cyclohexyl}-ethanol obtained with methanesulfonic acid chloride in the presence of an acid binding agent to give trans 2-{1-[4-(N-tert-butoxycarbonyl)-amino]-cyclohexyl}-ethyl methanesulfonate;
c) reacting trans 2-{1-[4-(N-tert-butoxycarbonyl)-amino]-cyclohexyl}-ethyl methanesulfonate obtained with 2,3-dichlorophenyl-piperazine in the presence of an acid binding agent to give trans 2-{1-[4-(N-tert-butoxycarbonyl)-amino]-cyclohexyl}-carbamic acid tert-butylester;
d) heating trans 2-{1-[4-(N-tert-butoxycarbonyl)-amino]-cyclohexyl}-carbamic acid tert-butylester obtained to a temperature between 40-100° C. in a mixture of aqueous hydrochloric acid/methanol to give trans N-{4-{2-[4-(2,3-dichlorophenyl)piperazine-1-il]-ethyl}-cyclohexylamine dihydrochloride monohydrate.

7 Claims, No Drawings

(56) References Cited

OTHER PUBLICATIONS

Aiken, "Pramipexole in psychiatry: A systematic review of the literature," *J. Clin Psychiatry.*, 68(8):1230-1236, (2007).
Baldessarini and Tarazi, "Pharmacotherapy of Psychosis and Mania," Brunton et al. (eds.), *Goodman and Gilman's The Pharmacological Basis of Therapeutics*, 11th Edition, McGraw Hill, Chapter 18, pp. 462-500, (2005).
Berge et al., "Pharmaceutical salts," *Journal of Pharmaceutical Sciences*, 66(1):1-19 (1977).
Bézard et al., "Attenuation of levodopa-induced dyskinesia by normalizing dopamine D3 receptor function," *Nat. Med.*, 9(6):762-767, (2003).
*Burger's Medicinal Chemistry and Drug Discovery.* vol. 1. Drug Discovery, 6th Edition. Wiley Interscience. Ed. Donald J. Abraham, ISBN 978-0-471-27090-4, Jan. 2003.
Creese et al., "Species variation in dopamine receptor binding," *Eur. J. Pharmacol.*, 60:55-66, (1979).
Damasio, "Alzheimer's Disease and Related Dementias," *Cecil Textbook of Medicine*, 20th Edition, vol. 2, pp. 1992-1996, (1996).
Dean, [Editor]. "Recent Advances in the Synthesis and Applications of Radiolabeled Compounds for Drug Discovery and Development," *Curr., Pharm. Des.*, vol. 6, No. 10, [Table of Contents] CAN 133:68895 AN 2000:473538 CAPLUS; 3 pages, (2000).
Di Chiara, "Drug addiction as dopamine-dependent associative learning disorder," *Eur. J. Pharmacol.*, 375: 13-30, (1999).
Eli Lilly and Company, "Zyprexa Olanzapine Tablets . . . ." MedWatch Safety Alerts for Human Medical Products, FDA [online]. Retrieved rom the Internet< URL:http://www.fda.gov/medwatch/safety/2006/Aug_Pls/Zyprexa_PI.pdf>, 31 pages, (2004).
Evans, "Synthesis of radiolabeled compounds," *J. Radioanal. Chem.*, 64(1-2):9-32, (1981).
Glase et al., "4-bromo-1-methoxy-N-[2-(4-aryl-1-piperazinyl)ethyl]-2-naphthalenecarboxamides: Selective dopamine D3 receptor partial agonists," *Bioorganic & Medicinal Chemistry Letters*, 6(12):1361-1366, (1996).
Goodwin and Jamison, In: *Manic-depressive illness*, New York: Oxford University Press, pp. 642-647, (1990).
Greengrass and Bremner, "Binding characteristics of 3H-prazosin to rat brain alpha-adrenergic receptors," *Eur. J. Pharmacol.*, 55(3):323-326, (1979).
Guérémy et al., "2-Amino-6-chloro-4-(N-methylpiperazino)pyrimidines, inhibitors of spiroperidol binding," *J. Med. Chem.*, 25(12):1459-1465, (1982).
Gurevich and Joyce, "Distribution of dopamine D3 receptor expressing neurons in the human forebrain: comparison with D2 receptor expressing neurons," *Neuropsychopharmacology*, 1999, 20:60-80.
Gurevich et al., "Mesolimbic dopamine D3 receptors and use of antipsychotics in patients with schizophrenia. A postmortem study." *Arch Gen Psychiatry.*, 54(3):225-232, (1997).
Guy, *ECDEU Assessment Manual for Psychopharmacology.* Rockville, Md: US Department of Health, Education, and Welfare, pp. 218-222, Publication ADM 76-338, (1976).
Gyertyan and Saghy, "Effects of dopamine $D_3$ receptor antagonists on spontaneous and agonist-reduced motor activity in NMRI mice and Wistar rats: comparative study with nafadotride, U 99194A and SB 277011," *Behavioural Pharamacology*, 15(4):253-262, (2004).
Gyertyán and Sághy, "The selective dopamine D3 receptor antagonists, SB 277011-A and S 33084 block haloperidol-induced catelepsy in rats," *Eur. J. Pharmacol.*, 572:171-174, (2007).
Gyertyán et al., "Subnanomolar dopamine D3 receptor antagonism coupled to moderate D2 affinity results in favourable antipsychotic-like activity: Behavioral Data," [abstract]. *Int. J. Neuropsychopharmacol.*, 5 Suppl. 1:174, 2002.
Heidbreder et al., "The role of central dopamine D3 receptors in drug addiction: a review of pharmacological evidence," *Brain Res. Rev.*, 49:77-105, (2005).
Janssen, "Risperdal Consta (risperidone) Long-Acting Injection," MedWatch Safety Alerts for Human Medical Products, FDA [online] Retrieved from the Internet:< URL:http://www.fda.gov/medwatch/safety/2006/Sep$_{13}$ Pls/RisperdalConsta_PI.pdf>, 39 pages (2006).
Joyce, "Dopamine D3 receptor as a therapeutic target for antipsychotic and antiparkinsonian drugs," *Pharmacol. Therap.*, 90:231-259, (2001).
Kabalka and Varma, "The synthesis of radiolabeled compounds via organometallic intermediates," *Tetrahedron*, 45(21):6601-6621, (1989).
Kay et al., "The positive and negative syndrome scale (PANSS) for schizophrenia," *Schizophr. Bull.*, 13:261-276, (1987).
Keck, "The management of acute mania," *British Medical Journal*, 327(7422):1002-1003, (2003).
King et al. (Oral solid dosage forms, in Remington's Pharmaceutical Sciences; Gennaro, A., Ed., 17th Edition, Mack Publishing Company, Easton PA, Chapter 90, pp. 1603-1632, (1985).
Laszy et al., "Dopamine D3 receptor antagonists improve the learning performance in memory impaired rats," *Psychopharmacol.*, 179(3):567-575, (2005).
Layzer, Degenerative Diseases of the Nervous System, *Cecil Textbook of Medicine*, 20th Edition, vol. 2, pp. 2050-2057, (1996).
Le Foll et al., "Dopamine D3 receptor ligands for the treatment of tobacco dependence," *Expert Opin Investig Drugs*, 16(1):45-57, (2007).
Lehman et al., "Practice guideline for the treatment of patients with schizophrenia, second edition," *Am. J. Psychiatry*, 161(2 Suppl):1-56, (2004).
Levant and McCarson, "D(3) dopamine receptors in rat spinal cord: implications for sensory and motor function," *Neurosci. Lett.*, 303:9-12 (2001).
Levant et al., "Dopamine $D_3$ receptor: relevance for the drug treatment of Parkinson's disease," *CNS Drugs*, 12:391-402, (1999).
Levant, "The D3 dopamine receptor: neurobiology and potential clinical relevance," *Pharmacol. Rev.*, 49(3):231-252, (1997).
Maj et al., "Effect of antidepressant drugs administered repeatedly on the dopamine D3 receptors in the rat brain," *Eur. J. Pharmacol.* 351:31-37, (1998).
Millan et al., "S33084, a novel, potent, selective, and competitive antagonist at dopamine D(3)-receptors: II. Functional and behavioral profile compared with GR218,231 and L741,626," *J. Pharmacol. Exp. Ther.*, 2000, 293:1063-1073.
Millan et al., "The dopamine D3 receptor antagonist, (+)-S 14297, blocks the cataleptic properties of haloperidol in rats," *Eur. J. Pharmacol.*, 321:R7-R9, (1997).
Montgomery and Asberg, "A new depression scale designed to be sensitive to change," *Br. J. Psychiatry*, 134:382-389, (1979).
Mueser and McGurk, "Schizophrenia," *Lancet*, 363:2063-2072, (2004).
Müller-Oerlinghausen et al., "Bipolar disorder," *Lancet*, 359(9302):241-247, (2002).
Nassar et al., "Improving the decision-making process in structural modification of drug candidates: reducing toxicity," *Drug Discov Today*, 9(24):1055-1064, (2004).
Nyberg et al., "Positron emission tomography of in-vivo binding characteristics of atypical antipsychotic drugs. Review of D2 and 5-HT2 receptor occupancy studies and clinical response," *Br. J. Psychiatry. Suppl.*, 29:40-44, (1996).
Pacher and Kecskeméti, "Cardiovascular side effects of new antidepressants and antipsychotics: new drugs, old concerns?" *Curr. Pharm. Des.*, 10(20):2463-2475, (2004).
Papp and Wieronska, "Antidepressant-like activity of amisulpride in two animal models of depression," *J. Psychopharmacol.*, 14:46-52, (2000).
Pilla et al., "Selective inhibition of cocaine-seeking behaviour by a partial dopamine D3 receptor agonist," *Nature*, 400:371-375, (1999).
Reavill et al., "Pharmacological actions of a novel, high-affinity, and selective human dopamine D(3) receptor antagonist, SB-277011-A," *A. J. Pharmacol. Exp. Ther.*, 294:1154-1165, (2000).
Rogóz et al., "Anxiolytic-like effect of nafadotride and PNU 99194A, dopamine D3 receptor antagonists in animal models," *Pol J Pharmacol.*, 52(6):459-462, (2000).
Russell, "Neurobiology of animal models of attention-deficit hyperactivity disorder," *J. Neurosci. Methods* 161:185-198, (2007).

(56) References Cited

OTHER PUBLICATIONS

Sachs, "Unmet clinical needs in bipolar disorder," *J. Clin. Psychopharmacol.*, 23(3 Suppl 1):S2-S8, (2003).
Sautel et al., "Nafadotride, a potent preferential dopamine D3 receptor antagonist, activates locomotion in rodents," *J. Pharmacol. Exp. Ther.*, 1995, 275:1239-1246.
Schwartz et al., "Dopamine D3 receptor: basic and clinical aspects," *Clin. Neuropharmacol.*, 16(4):295-314, (1993).
Schwartz et. al., "Possible implications of the dopamine D(3) receptor in schizophrenia and in antipsychotic drug actions," *Brain Res. Rev.*, 31(2-3):277-287, (2000).
Seeman, "Antipsychotic drugs, dopamine receptors and schizophrenia," *Clin. Neurosci. Res.*, 1:53-60, (2001).
Seeman, "Brain dopamine receptors" *Pharmacological Reviews*, 32(3): 229-313 (1980).
Shafer and Levant, "The D3 dopamine receptor in cellular and organismal function," *Psychopharmacology* (Berl), v, 135:1-16, 1998.
Shalev et al., "Neurobiology of relapse to heroin and cocaine seeking: a review.," *Pharmacol. Rev.* 54 (1), 1-42, (2002).
Sigala et al., "Opposite effects of dopamine $D_2$ and $D_3$ receptors on learning and memory in the rat," *Eur. J. Pharmacol.*, 336:107-112, (1997).
Smith et al., "The dopamine D3/D2 receptor agonist 7-OH-DPAT induces cognitive impairment in the marmoset," *Pharmacol. Biochem. Behav.*, 63:201-211, (1999).
Sokoloff et al., "Molecular cloning and characterization of a novel dopamine receptor (D3) as a target for neuroleptics," *Nature*, 347:146-151, (1990).
Souillac, et al., Characterization of Delivery Systems, Differential Scanning Calorimetry, pp. 217-218 (in Encyclopedia of Controlled Drug Delivery, 1999, John Wiley & Sons, pp. 212-227), (1999).
Stahl and Grady, "A critical review of atypical antipsychotic utilization: comparing monotherapy with polypharmacy and augmentation," *Curr. Med. Chem.*, 11:313-327, (2004).
Stahl, *Essential Psychopharmacology: Neuroscientific Basis and Practical Applications*, 2nd ed., p. 409, Cambridge University Press, pp. 409-414, (2000).
Steiner et al., "D3 dopamine receptor-deficient mouse: evidence for reduced anxiety," *Physiol Behav.*, 63(1):137-141, (1997).
Stemp et al., "Design and synthesis of trans-N-[4-[2-(6-cyano-1,2,3, 4-tetrahydroisoquinolin-2-yl)ethyl]cyclohexyl]-4-quinolinecarboxamide (SB-277011): A potent and selective dopamine D(3) receptor antagonist with high oral bioavailability and CNS penetration in the rat," *J. Med. Chem.*, 43(9):1878-1885, (2000).
Tada et al., "Combined treatment of quetiapine with haloperidol in animal models of antipsychotic effect and extrapyramidal side effects: comparison with risperidone and chlorpromazine," *Psychopharmacology* (Berl), 176(1):94-100, (2004).
Thanos et al., "The effects of two highly selective dopamine D3 receptor antagonists (SB-277011A and NGB-2904) on food self-administration in a rodent model of obesity," *Pharmacol Biochem Behav.* 89: 499-507, (2008).
Ukai et al., "Effects of the dopamine D3 receptor agonist, R(+)-7-hydroxy-N,N-di-n-propyl-2-aminotetralin, on memory processes in mice," *Eur. J. Pharmacol.*, 324:147-151, (1997).
Ulrich, Chapter 4: Crystallization, *Kirk-Othmer Encyclopedia of Chemical Technology*, 7 pages, (2002).
van der Kooij and Glennon, "Animal models concerning the role of dopamine in attention-deficit hyperactivity disorder," *Neuroscience and Biobehavioral Reviews*, 31: 597-618, (2007).
Waters et al., "Differential effects of dopamine D2 and D3 receptor antagonists in regard to dopamine release, in vivo receptor displacement and behavior," *J. Neural. Transm. Gen. Sect.*, 98:39-55, (1994).
West, *Solid State Chemistry and Its Applications*, Wiley, pp. 358, (1988).
Willner et al., "Dopaminergic mechanism of antidepressant action in depressed patients," *J. Affective Disorders* 86: 37-45, (2005).
Wong and Van Tol, "Schizophrenia: from phenomenology to neurobiology," *Neurosci. Biobehav. Rev.*, 27(3):269-306, (2003).
World Health Organization, World Health Report 2001, "Mental Health: New Understanding, New Hope." http://www.who.int/whr/2001/en/2001, (2001).
Wyatt and Henter, "An economic evaluation of manic-depressive illness—1991," *Soc. Psychiatry Psychiatr. Epidemiol.*, 30(5):213-219, (1995).
Youdim, "The path from anti Parkinson drug selegiline and rasagiline to multifunctional neuroprotective anti Alzheimer drugs ladostigil and m30," *Curr Alzheimer Res.*, 3(5):541-550, 2006.
Young, et al., "A rating scale for mania: reliability, validity and sensitivity," *The British Journal of Psychiatry*, 133:429-435, (1978).
Zink et al., "Combination of amisulpride and olanzapine in treatment-resistant schizophrenic psychoses," *Eur. Psychiatry*, 19:56-58, (2004).
International Search Report for PCT/HU2009/000108, mailed Mar. 17, 2010, 3 pages.
International Preliminary Report on Patentability and Written Opinion for PCT/HU2009/000108, issued Jun. 21, 2011, 6 pages.
Belliotti, et al., "Novel cyclohexyl amides as potent and selective D3 dopamine receptor ligands", 19970000, vol. 7, No. 18, Jan. 1, 1997pp. 2403-2408.
EPO Search Report dated Mar. 11, 2010, mailed Mar. 17, 2010, Authorized officer Menegaki, Fotini.
Nassar et al; Improving the decision-making process in structural modification of drug candidates: reducing toxicity; Drug Discov Today; Dec. 2004; 9(24):1055-1064.
Nassar et al; Improving the decision-making process in the structural modification of drug candidates: enhancing metabolic stability; Drug Discov Today; Dec. 2004; 9(23)1020-1028.
Pacher and Kecskeméti; Cardiovascular side effects of new antidepressants and antipsychotics: new drugs, old concerns?; Curr. Pharm. Des.; 2004; 10(20):2463-2475.
Vippagunta et al; Crystalline Solids; Advanced Drug Delivery Reviews; 2001; 48(1):3-26.
Morissette et al; High-throughput crystallization: polymorphs, salts, co-crystals and solvates of pharmaceutical solids; Adv Drug Deliv Rev; Feb. 2004; 56(3):275-300.

\* cited by examiner

PIPERAZINE SALT AND A PROCESS FOR THE PREPARATION THEREOF

CROSS-REFERENCE TO RELATED APPLICATIONS

This application is a National Stage application under 35 U.S.C. §371 of International Application No. PCT/HU2009/0000108, having an International Filing Date of Dec. 17, 2009, which claims the benefit of priority of HU Application No. P08 00763, having a filing date of Dec. 17, 2008, all of which are incorporated herein in their entirety.

FIELD OF THE INVENTION

The present invention relates to novel trans {4-{2-[4-(2,3-dichlorophenyl)-piperazine-1-il]-ethyl}-cyclohexylamine dihydrochloride monohydrate and to a process for the preparation thereof.

BACKGROUND OF THE INVENTION

The trans {4-{2-[4-(2,3-dichlorophenyl)-piperazine-1-il]-ethyl}-cyclohexylamine dihydrochloride monohydrate according to the invention is a key intermediate for the preparation of a number of compounds acting on $D_3/D_2$ receptor. Similar compounds were described in the Hungarian Patent Specifications No. P0103988 and P0302451, and in Bioorg. Med. Chem. Lett. EN; 7; 18; 1997 2403-2408.

The Hungarian Patent Specification No. P0103988 discloses a reaction route for the preparation of trans {4-{2-[4-(2,3-dichlorophenyl)-piperazine-1-il]-ethyl}-cyclohexylamine dihydrochloride. According to the preparation process described in Example 1, 2,3-dichlorophenyl-piperazine and trans 2-{1-[4-(N-terc-butoxycarbonyl)-amino]-cyclohexyl}-acetaldehyde are dissolved and coupled in dichloromethane in the presence of sodium triacetoxy borohydride to give trans N-{4-{2-[4-(2,3-dichlorophenyl)-piperazine-1-il]-ethyl}-cyclohexyl}-carbamic acid tertiary butylester. Then the protective group is removed in ethyl acetate by hydrochloride acid according to a process described in Example 2. The yield data for trans N-{4-{2-[4-2,3-dichlorophenyl)-piperazine-1-il]-ethyl}-cyclohexyl}-carbamic acid tertiary butylester or for trans N-{4-{2-[4-(2,3-dichlorophenyl)-piperazine-1-il]-ethyl}-cyclohexyl}-amine dihydrochloride are not described either.

The drawback of the above procedure is that when preparing trans 2-{1-[4-(N-tert-butoxycarbonyl)-amino]-cyclohexyl}-acetaldehyde from the corresponding trans 2-{1-[4-(N-tert-butoxycarbonyl)-amino]-cyclohexyl}-acetic acid ester the reaction can be carried out at a temperature below 70° C. and with only 55% yield (Stemp et al. J. Med. Chem. 2000. Vol. 43, No. 9, p. 7878-7885). However, use of the above operating temperature and the very hazardous diisobutyl aluminium hydride mean technological problems in industrial scale therefore the reaction can be carried out only in extra equipments and at extreme conditions.

The procedure disclosed in the above mentioned Bioorg. Med. Chem. Lett. EN; 7; 18; 1997 2403-2408 literature consists of eight reaction steps and the compounds are mentioned only in general without any characterizing features. The eight steps procedure seems to be complicated, expensive and hazardous particularly performing in industrial scale.

Our aim was to provide a safe and in industrial scale easy-to-manage process for the preparation of trans N-{4-{2-[4-(2,3-dichlorophenyl)-piperazine-1-il]-ethyl}-cyclohexylamine key intermediate by which it can be prepared in good yield via simple reaction steps without using extreme reaction conditions and extra equipments.

BRIEF DESCRIPTION OF THE INVENTION

In the course of our experiences, we have surprisingly found, that starting from trans 2-{1-(4-N-[tert-butoxycarbonyl]amino)-cyclohexyl}-acetic acid ester and using the economical process according to the invention the trans 4-{2-[4-(2,3-dichlorophenyl)-piperazine-1-il]-ethyl}-cyclohexylamine dihydrochloride monohydrate can be produced by four easy-to-make and economical synthesis steps in high purity at industrial scale wherein all of the steps can be carried out with good yields.

In the first reaction step trans 2-{1-(4-[N-tert-butoxycarbonyl]amino)-cyclohexyl}-acetic acid ester is converted to trans-2-{1[4-(N-tert-butoxycarbonyl)-amino]-cyclohexyl}-ethyl alcohol quantitatively by using sodium borohydride and aluminium trichloride. In the following reaction step the trans 2-{1-[4-(N-tert-butoxycarbonyl)-amino]cyclohexyl}-ethyl alcohol obtained in step 1 is reacted with methanesulfonyl chloride to give mesylester, then the mesylester is reacted with 2,3-dichlorophenylpiperazine in the presence of an acid binding agent. In the last step the protecting group is removed under simple reaction conditions in a mixture of water/hydrochloric acid/methanol at a temperature of 40-100° C. to give trans N-{4-{2-[4-(2,3-dichlorophenyl)-piperazine-1-il]-ethyl}-cyclohexylamine dihydrochloride monohydrate in very high purity and good yield.

DETAILED DESCRIPTION OF THE INVENTION

In the first reaction step trans 2-{1-[4-(N-tert-butoxycarbonyl)-amino]-cyclohexyl}-acetic acid ester is converted to trans 2-{1-[4-(N-terc-butoxycarbonyl)-amino]-cyclohexyl}-ethyl alcohol. It is well known to those skilled in the art that the above reaction may be carried out only at law (−40° C.) temperature and in the presence of the very hazardous lithium aluminium hydride. In our experiments we have surprisingly found that when the reaction is performed in an ether solvent, for example in THF at a temperature between 0-30° C., preferably between 5-25° C. in the presence of sodium borohydride and aluminium trichloride, the trans 2-{1-[4-(N-tert-butoxycarbonyl)-amino]-cyclohexyl}-ethyl alcohol is obtained with almost quantitative yield.

In the second reaction step the trans 2-{1-[4-(N-tert-butoxycarbonyl)-amino]-cyclohexyl}-ethyl alcohol obtained in step 1 is treated with methanesulfonyl chloride in the presence of an acid binding agent to give mesylester. Optionally the reaction may be carried out without isolation of the starting trans 2-{1-[4-(N-tert-butoxycarbonyl)-amino]-cyclohexyl}-ethyl alcohol. Suitable acid binding agents, which can be used in this reaction step, include inert organic bases, preferably inert organic amines, more preferably triethylamine. Suitable solvents which can be used include inert water-immiscible solvents, for example toluene, dichloromethane, chlorobenzene or xylene, preferably dichloromethane. The efficiency of the reaction is almost quantitative.

In the following step trans 2-{1-[4-(N-tert-butoxycarbonyl)-amino]-cyclohexyl}-ethyl methanesulfonate is reacted with 2,3-dichlorophenyl-piperazine in the presence of an acid binding agent to obtain trans {4-[2-[4-(2,3-dichlorophenyl)-piperazine-1-yl]-ethyl]-cyclohexyl}-carbaminic acid tert-butyl ester. As an optional route, the reaction may be carried out without isolation of the starting trans 2-{1-[4-(N-tert-butoxycarbonyl)-amino]-cyclohexyl}-ethyl methanesulfonate. As acid binding agent alkali bases, for example alkali carbonates, preferably potassium carbonate is employed. Suitable solvents, which can be used in this reaction step, include inert water-immiscible solvents, for example toluene, dichloromethane, chlorobenzene or xylene, preferably dichloromethane. The yield is higher than 80%.

In a preferred embodiment of the invention the above three reaction steps are reduced to one step and the reaction is carried out in one reaction vessel without isolation of the intermediate compounds. In this case there is no need to clean the equipments in costly separate steps. In this manner the total yield is higher than 70% based on the starting material, hereby increasing the economical efficiency of the procedure.

In the last reaction step the N-tert-butoxycarbonyl protecting group is removed in a mixture of aqueous hydrochloric acid and methanol at a temperature between 40-400° C., preferably between 45-50° C. to give a crystalline product, which proves the new dihydrochloride monohydrate form of trans N-{4-{2-[4-(2,3-dichlorophenyl)-piperazine-1-il]-ethyl}-cyclohexyl}-amine. We have surprisingly found, that performing the reaction in the presence of water, the trans N-{4-{2-[4-(2,3-dichlorophenyl)-piperazine-1-il]-ethyl}-cyclohexyl}-amine dihydrochloride monohydrate is obtained almost quantitatively in high purity and the yield is higher than 99%.

The invention is illustrated by the following non-limiting Examples.

Example 1

Preparation of trans 2-{1-[4-(N-tert-butoxycarbonyl)-amino]-cyclohexyl}-acetic acid ethyl ester An 500 ml four-necked flask is charged with 40 g (0.18 mol) of trans 2[1-(4-amino]-cyclohexyl)-acetic acid ethyl ester and 160 ml of dichloromethane, then 18.2 g (0.18 mol) of triethylamine is added. The reaction mixture obtained is cooled to a temperature between 5-10° C. then a solution of 40.0 g (0.18 mol) of di(tert-butyl)dicarbonate in 100 ml of dichloromethane is added for 1 hour with stirring under nitrogen. Then the reaction mixture is allowed to warm to room temperature and stirred until the reaction proceeds. After completion of the reaction 100 g of 5% aqueous sodium carbonate is added and the phases are separated. The organic layer is washed with 50 ml of water and after separation the organic layer is dried under $Na_2SO_4$ and the filtrate is concentrated to 40 ml in vacuum. The thick crystalline suspension obtained is poured into a platter and dried under infra-red lamp at up to 35° C.

In this manner 47.9 g of title compound was obtained.
Yield: 93%
Melting point: 73-74° C.

Example 2

Preparation of trans 2-{1-[4-(N-tert-butoxycarbonyl)-amino]-cyclohexyl}ethanol

An 500 ml four-necked flask is charged with 40 g (0.18 mol) of trans 2-[1-(4-amino]-cyclohexyl)-acetic acid ethyl ester hydrochloride and 160 ml of dichloromethane. To the resulting suspension 18.2 g (0.18 mol) of triethylamine is added. The reaction mixture is cooled to a temperature between 8-10° C. and a solution of 40.0 g (0.185 mol) of di(tert-butyl)dicarbonate in 100 ml of dichloromethane is added for 1 hour with stirring under nitrogen. Then the reaction mixture is allowed to warm to a temperature between 22-25° C. and stirred until the reaction proceeds. After completion of the reaction 100 g of 5% aqueous sodium carbonate is added and the phases are separated. The organic layer is extracted with 50 ml of water and after separation the organic layer is dried under $Na_2SO_4$ and the filtrate is concentrated in vacuum. The trans 2-{1-[4-(N-tert-butoxycarbonyl)-amino]-cyclohexyl}-acetic acid ethyl ester obtained is dissolved in 460 ml of tetrahydrofurane then 13.68 g (0.36 mol) of sodium borohydride is added at 25° C. under nitrogen. With stirring, to the reaction mixture a solution of 24.0 g (0.18 mol) of aluminium chloride in 250 ml abs. tetrahydrofurane is added dropwise at a temperature between 18-22° C. for 1 hour under nitrogen then the mixture is stirred for additional 2 hours. After completion of the reaction the mixture is cooled to a temperature between 5-10° C. and 650 ml of water and 600 ml of toluene are added. Then the pH was adjusted to 3-4 by adding 40-45 ml of concentrated hydrochloric acid and the stirring was continued at a temperature between 20-25° C. for 1 hour. The phases are separated, the aqueous layer is extracted with 50 ml of toluene and the combined organic layers are washed with 3×150 ml of water and dried in vacuum.

In this manner 41.1 g of title compound was obtained.
Yield: 94%
Melting point: 101-103° C.

Example 3

Preparation of trans 2-{1-[4-(N-tert-butoxycarbonyl)-amino]-eyelohexyl}-ethyl methanesulfonate With stirring 37 g (0.15 mol) of trans 2-{1[4-(N-tert-butoxycarbonyl)-amino]-cyclohexyl}-ethanol is dissolved in 360 ml of dichloromethane at a temperature between 20-25° C. and 19.6 g (0.19 mol) of triethylamine is added. The solution obtained is cooled to a temperature between 0-5° C. and a solution of methanesulfonyl chloride in dichloromethane is added dropwise. Then the stirring is continued for further 1 hour while the temperature is maintained between 0-5° C. and the pH is kept at 8-9 by adding triethylamine. After completion of the reaction 450 ml water is added and after stirring for 15 minutes the phases are separated. The aqueous phase is extracted with 30 ml of dichloromethane then the combined organic phases are washed with 3×300 ml of water and the dichloromethane solution is concentrated in vacuum.

In this manner 46.2 g of title compound was obtained.
Yield: 90%
Melting point: 112-113° C.

Example 4

Preparation of trans N-tert-butoxycarbonyl-4-{2-[4-(2,3-dichlorophenyl)-piperazine-1-yl]-ethyl}-cyclohexylamine 48 g (0.15 mol) of trans 2-{1-[4-(N-tert-butoxycarbonyl)-amino]-cyclohexyl}-ethyl methanesulfonate is suspended in 800 ml of acetonitrile. To the suspension obtained 75 g (0.28 mol) of 1-(2,3-dichlorophenyl)-piperazine hydrochloride and 71.8 g (0.56 mol) of potassium carbonate are added and the reaction mixture is heated to reflux and stirred for 15-17 hours. After completion of the reaction the mixture is cooled to a temperature between 45-50° C. and 900 ml of water is added. With stirring the temperature is brought to room temperature and the stirring is continued for further 1.5 hours. The product separated is filtered and washed with water until pH neutral. Then a solution of 400 ml of water and 7 ml of concentrated hydrochloric acid is added and the mixture is stirred for 2 hours at a temperature between 20-25° C. and filtered then washed with 15-20 ml of water. To the crude product obtained 540 ml of acetonitrile is added and the reaction mixture is heated to reflux and stirred for 15 minutes. The mixture is cooled to a temperature between 0-5° C. and the stirring is continued for 1 hour while the temperature is maintained at this level. The precipitated product is filtered, washed with 10 ml of cold acetonitrile and dried.

In this manner 54.7 g of title compound was obtained.
Yield: 80%
Melting point: 150-154° C.

Example 5

Preparation of trans N-tert-butoxycarbonyl-4-{2-[4-(2,3-dichlorophenyl)-piperazine-1-yl]-ethyl}-cyclohexylamine An 1 l four-necked round bottom flask is charged with 42.9 g (0.15 mol) of trans 2-{1-[4-(N-tert-butoxycarbonyl)-amino]-cyclohexyl}-acetic acid ethyl ester and 400 ml of tetrahydrofurane and to the solution obtained 11.4 g (0.3 mol) of sodium borohydride is added at 25° C. temperature under nitrogen. To the stirred reaction mixture a solution of 20.0 g (0.15 mol) of aluminium chloride in 225 ml abs. tetrahydrofurane is added dropwise at a temperature between 18-22° C. for 1 hour under nitrogen, then the stirring is continued for additional 2 hours. After ending the reaction the mixture is cooled to a temperature between 5-10° C. and 650 ml of water then 450 ml of toluene are added and the pH is adjusted to 3-4 by adding 30-40 ml of concentrated hydrochloric acid. Stirring is continued for 1 hour at a temperature between 20-25° C. The phases are separated, the aqueous layer is extracted with 50 ml of toluene, and the combined organic layers are washed with 3×150 ml of water and concentrated to about 50 ml volume in vacuum. To the concentrated stirred solution 360 ml of dichloromethane and 19.6 g (0.19 mol) of triethylamine are added at a temperature between 20-20° C. The solution is then cooled to a temperature between 0-5° C. and a solution of 19.7 g (0.17 mol) of methanesulfonyl chloride in 90 ml of dichloromethane is added dropwise over 1 hour and the reaction mixture is stirred for further 1 hour. The pH is maintained at 8-9 by adding triethylamine. After completion of the reaction 450 ml of water is added and the mixture is stirred for 15 minutes then the phases are separated. The aqueous layer is extracted with 30 ml of dichloromethane then the combined organic layers are washed with 3×300 ml of water. The dichloromethane solution is concentrated to about 70 ml volume under vacuum then 900 ml of acetonitrile is added and about 80-100 ml solvent is distilled off under vacuum. The residue obtained is cooled to a temperature between 20-25° C. and 75 g (0.28 mol) of 1-(2,3-dichlorophenyl)-piperazine hydrochloride and 71.8 g (0.56 mol) of potassium carbonate are added then the mixture is heated to reflux and stirred for 15-16 hours. After ending the reaction the mixture is cooled to a temperature between 45-50° C. and 900 ml of water is added then the stirred mixture is cooled to room temperature. The stirring is continued for further 1.5 hours during which the temperature is kept at this level. The product obtained is filtered off and washed with water until pH neutral then a solution of 400 ml of water and 7 ml of concentrated hydrochloric acid is added. After stirring at a temperature between 20-25° C. for 2 hours the product obtained is filtered and washed with water. To the resulting crude product 540 ml of acetonitrile is added and the mixture obtained is heated to reflux and stirred for 15 minutes, then cooled to a temperature between 0-5° C. The stirring is continued for another 1 hour maintaining temperature between 0-5° C. The product precipitated is filtered off and washed with 10 ml of cold acetonitrile then dried.

In this manner 51.3 g of title compound was obtained.
Yield: 75%
Melting point: 150-154° C.

Example 6

Preparation of trans N-tert-butoxycarbonyl-4-{2-[4-(2,3-dichlorophenyl)-piperazine-1-yl]-ethyl}-cyclohexylamine A 500 ml four-necked round bottom flask is charged with 40 g (0.18 mol) of trans 2-[1-(4-aminocyclohexyl)-acetic ethyl ester hydrochloride and 160 ml of dichloromethane and to the resulting suspension 18.2 g (0.18 mol) of triethylamine is added. The mixture obtained is cooled to a temperature between 0-10° C. and with stirring a solution of 40.0 g (0.185 mol) of di(tert-butyl dicarbonate) in 100 ml of dichloromethane is added for one hour under nitrogen. The reaction mixture is then allowed to warm to a temperature between 20-25° C. and the stirring is continued until the reaction proceeds. After completion of the reaction 100 g of 5% aqueous sodium carbonate solution is added then the phases are separated. The organic layer is extracted with 50 ml of water and after separating the organic layer is dried on $Na_2SO_4$ and the solvent is removed under vacuum.

The trans 2-{1-[N-tert-butoxycarbonyl)-amino]-cyclohexyl}-acetic ethyl ester obtained is dissolved in 468 ml of tetrahydrofurane then 13.68 g (0.36 mol) of sodium borohydride is added at 25° C. temperature under nitrogen. To the stirred reaction mixture a solution of 24.0 g (0.18 mol) of aluminium chloride in 270 ml of absolute tetrahydrofurane is added dropwise over 1 hour at a temperature between 18-22° C. and the stirring is continued for about 2 hours. The reaction mixture is then cooled to a temperature between 5-10° C. and 650 ml of water and 600 ml of toluene are added and the pH is adjusted to 3-4 by adding concentrated hydrochloric acid. After stirring at a temperature between 20-25° C. for 1 hour, the phases are separated and the aqueous layer is extracted with 50 ml of toluene. The combined organic extracts are washed with 3×150 ml of water and the mixture is concentrated to 60 ml volume under vacuum. To the stirred concentrated solution 430 ml of dichloromethane and 23.5 g (0.23 mol) of triethylamine are added at a temperature between 20-25° C. The solution obtained is cooled to 0-5° C. temperature and a solution of 23.6 g (0.2 mol) of methanesulfonic chloride in 110 ml of dichloromethane is added dropwise over 1 hour. The reaction mixture is stirred for 1 hour maintaining the temperature at 0-5° C. The pH is maintained at 8-9 by adding triethylamine. After ending the reaction 500 ml of water is added and after stirring for 15 minutes the phases are separated. The aqueous layer is extracted with 50 ml of water and the combined organic layers are washed with 3×300 ml of water. The dichloromethane solution is concentrated to about 80 ml volumes under vacuum and 1 l of acetonitrile is added, then about 80-100 ml of solvent are distilled of under vacuum. The mixture obtained is cooled to a temperature between 20-25° C. and 80 g (0.3 mol) of 1-(2,3-dichlorophenyl)-piperazine and 82.8 g (0.6 mol) of potassium carbonate are added. The reaction mixture is heated to reflux and stirred for 15-17 hours. The mixture is then cooled to 45-50° C. and 1 l of water is added with stirring and the mixture is cooled to room temperature and the stirring is continued for further 1.5 hours. The product precipitated is filtered and washed with water until pH neutral and a solution of 400 ml of water and 7 ml of concentrated hydrochloric acid is added. The mixture obtained is stirred for 2 hours at a temperature between 20-25° C. and the product is filtered and washed with water. To the crude product obtained 600 ml of acetonitrile is added and the mixture is stirred under reflux for 15 minutes, then cooled to 0-5° C. and the stirring was continued for further 1 hour. The product precipitated is filtered, washed with 10 ml of cold acetonitrile and dried.

In this manner 57.5 g of title compound was obtained.
Yield: 70%
Melting point: 150-154° C.

Example 7

Preparation of trans 4-{2-[-(2,3-dichlorophenyl)-piperazine-1-yl]-ethyl}-cyclohexylamine dihydrochloride monohydrate A 500 ml 3-necked round bottom flask is charged with 22 g (0.05 mol) of trans N-tert-butoxycarbonyl-4-{2-[4-(2,3-dichlorophenyl)-piperazine-1-yl]-ethyl}-cyclohexylamine and 150 ml of ethanol. To the stirred mixture a solution of 37.2 ml concentrated hydrochloric acid in 113 ml of water is added and the mixture is heated to a temperature between 45-50° C. and the stirring is continued for 2 hours maintaining the same temperature. After ending the reaction 120-140 ml of aqueous methanol is distilled off and the resulting mixture is cooled to room temperature and further to a temperature between 5-10° C. with stirring and the stirring is continued for 1 hour at the same temperature. The product precipitated is filtered and dried.

In this manner 21.5 g of title compound was obtained.
Yield: 94%
Melting point: over 310° C. (destroy).

The invention claimed is:

1. Trans N-{4-{2-[4-(2,3-dichlorophenyl)-piperazine-1-yl]-ethyl}-cyclohexylamine dihydrochloride monohydrate.

2. A process for the preparation of trans N-{-4-{2-[4-(2,3-dichlorophenyl)-piperazine-1-yl]-ethyl}-cyclohexylamine dihydrochloride monohydrate comprising
   a) reacting trans 2-{1-[4-(N-tert-butoxycarbonyl)amino]-cyclohexyl}-acetic acid ethyl ester with sodium borohydride and aluminium trichloride to give trans 2-{1-[4-(N-tert-butoxycarbonyl)-amino]-cyclohexyl}-ethanol;
   b) reacting trans 2-{1-[4-(N-tert-butoxycarbonyl)-amino]cyclohexyl}-ethanol obtained with methanesulfonic acid chloride in the presence of an acid binding agent to give trans 2-{1-[4-(N-tert-butoxycarbonyl)-amino]-cyclohexyl}-ethyl methanesulfonate;
   c) reacting trans 2-{1-[4-(N-tert-butoxycarbonyl)-amino]-cyclohexyl}-ethyl methanesulfonate obtained with 2,3-dichlorophenyl-piperazine in the presence of an acid binding agent to give trans N-tert-butoxycarbonyl-4-{2-[4-(2,3-dichlorophenyl)-piperazine-1-yl]-ethyl}-cyclohexylamine; and
   d) heating trans N-tert-butoxycarbonyl-4-{2-[4-(2,3-dichlorophenyl)-piperazine-1-yl]-ethyl}-cyclohexylamine obtained to a temperature between 40-100° C. in a mixture of aqueous hydrochloric acid/methanol to give trans N-{4-{2-[4-(2,3-dichlorophenyl)piperazine-1-yl]-ethyl}-cyclohexylamine dihydrochloride monohydrate.

3. The process according to claim 2 characterized in that the steps a) and b) are carried out without isolation of the intermediate compounds obtained.

4. The process according to claim 2 characterized in that in step b) organic amines are employed as acid binding agent.

5. The process according to claim 4 characterized in that in step b) triethylamine is employed as acid binding agent.

6. The process according to claim 2 characterized in that in step c) an alkali carbonate is employed as acid binding agent.

7. The process according to claim 2 characterized in that in step d) heating is made at a temperature between 45-50° C.

* * * * *

UNITED STATES PATENT AND TRADEMARK OFFICE
CERTIFICATE OF CORRECTION

PATENT NO.          : 8,569,496 B2
APPLICATION NO.     : 13/140232
DATED               : October 29, 2013
INVENTOR(S)         : Laszlo Czibula et al.

It is certified that error appears in the above-identified patent and that said Letters Patent is hereby corrected as shown below:

Title Page 2, Column 1, line 27 References Cited (Other Publications), delete "rom the" and insert -- from the --, therefor;

Title Page 2, Column 1, line 56 References Cited (Other Publications), delete "Pharamacology," and insert -- Pharmacology, --, therefor;

Title Page 2, Column 1, line 59 References Cited (Other Publications), delete "catelepsy" and insert -- catalepsy --, therefor;

In the Claims

Column 7, line 36 (Claim 1), delete "N-{4-" and insert -- N-4- --, therefor;

Column 8, line 1 (Claim 2), delete "N-{-4-" and insert -- N-4- --, therefor;

Column 8, line 24 (Claim 2), delete "N-{4-" and insert -- N-4- --, therefor.

Signed and Sealed this
First Day of July, 2014

Michelle K. Lee
*Deputy Director of the United States Patent and Trademark Office*